United States Patent [19]
Marlow et al.

[11] Patent Number: 5,563,384
[45] Date of Patent: Oct. 8, 1996

[54] BULK DENSITY SAMPLER APPARATUS

[75] Inventors: Brian S. Marlow, Lawrence, Kans.; Ronald J. Roman, Winfield; Robert Stanton, St. Louis, both of Mo.

[73] Assignee: III Sigma Company, Lawrence, Kans.

[21] Appl. No.: 219,075

[22] Filed: Mar. 28, 1994

[51] Int. Cl.$^6$ .......................... G01G 19/52; G01G 19/00; G01N 9/02
[52] U.S. Cl. .......................... 177/50; 73/863.51; 73/433; 177/145
[58] Field of Search .......................... 73/863.51, 863.52, 73/433; 141/83; 177/50, 25.13, 4, 45, 6, 3, 2, 229, 145

[56] References Cited

U.S. PATENT DOCUMENTS

| | | |
|---|---|---|
| 1,222,919 | 4/1917 | Bennett . |
| 2,683,373 | 7/1954 | Gallup et al. . |
| 3,076,341 | 2/1963 | Murray et al. . |
| 3,181,369 | 5/1965 | Taylor . |
| 3,250,131 | 5/1966 | Jordison . |
| 3,267,737 | 8/1966 | Biebighauser . |
| 3,282,116 | 11/1966 | Jones . |
| 3,768,510 | 10/1973 | Reves .................................. 137/551 |
| 4,218,920 | 8/1980 | John, Jr. .................................. 73/433 |
| 4,326,425 | 4/1982 | Gundersen et al. .................. 73/863.53 |
| 4,518,699 | 5/1985 | Bohl .................................. 177/25.11 X |
| 4,562,044 | 12/1985 | Bohl .................................. 177/145 X |
| 4,630,696 | 12/1986 | Kemnitz .................................. 177/165 |
| 4,766,964 | 8/1988 | Hirota et al. .................................. 177/25.11 |
| 5,072,624 | 12/1991 | Montgomery .................. 73/863.91 |
| 5,121,641 | 6/1992 | Silver .................................. 73/863.52 |
| 5,127,450 | 7/1992 | Saatkamp .................................. 141/83 X |
| 5,300,736 | 4/1994 | Ehrhardt .................................. 177/145 |

*Primary Examiner*—Brian W. Brown
*Assistant Examiner*—Randy W. Gibson
*Attorney, Agent, or Firm*—Hovey, Williams, Timmons & Collins

[57] ABSTRACT

Improved bulk density sampler is provided for continuous sampling of material flowing in a material processing stream which includes a sampling assembly including a receptacle of known volume mounted on and secured to a load cell configured to selectively measure the assembly weight both when the sampling assembly receptacle is full and empty. Preferably, the bulk density sampler includes a housing for protection of the sampling assembly and receptacle from product stream and other debris which may be present in the operating environment during the weight measurement. The bulk density sampler also preferably includes a programmable controller which controls the operation of the bulk density sampler and provides additional functionalities such as trend chart analysis, alarm functions, and sampling frequencies.

25 Claims, 2 Drawing Sheets

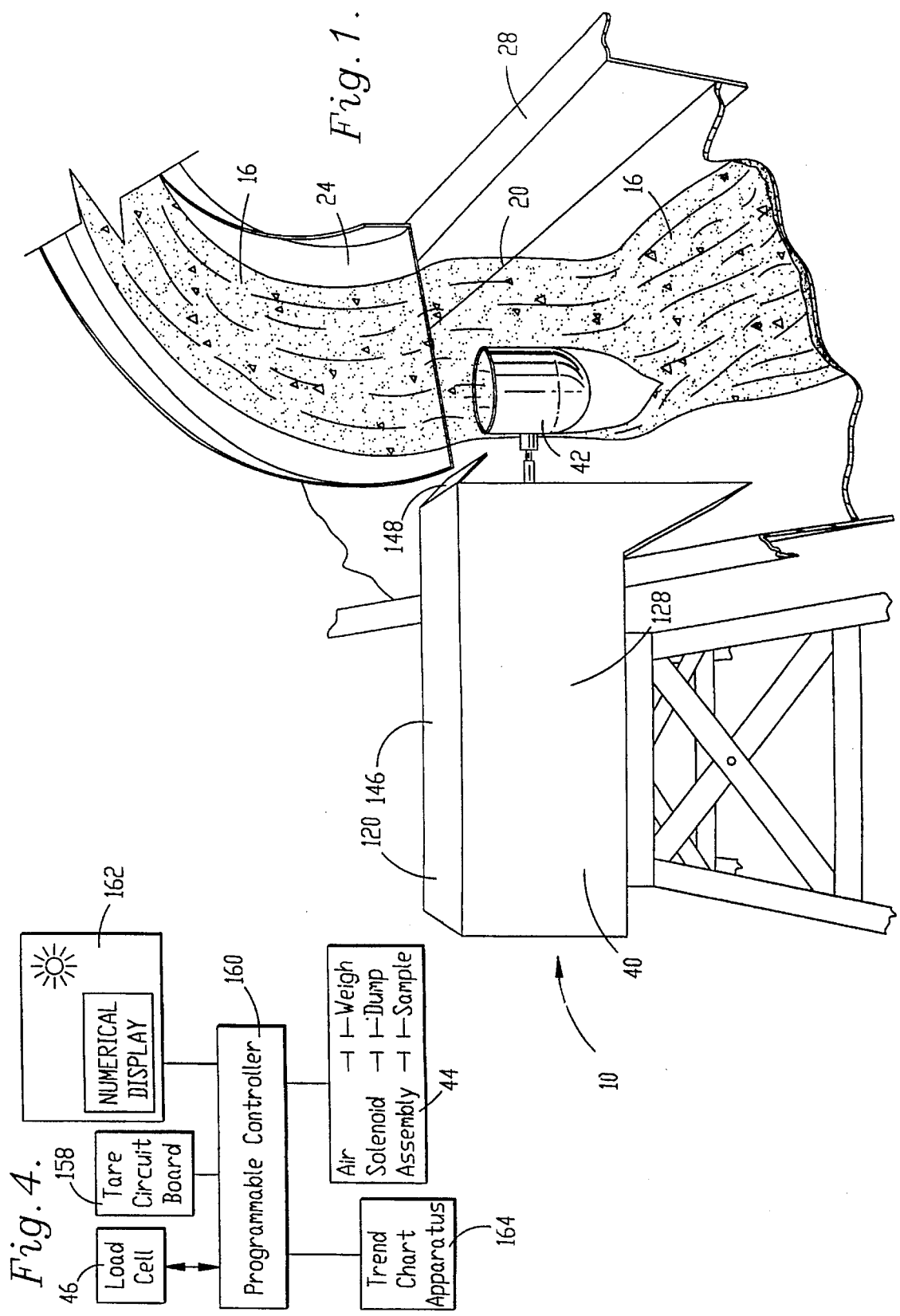

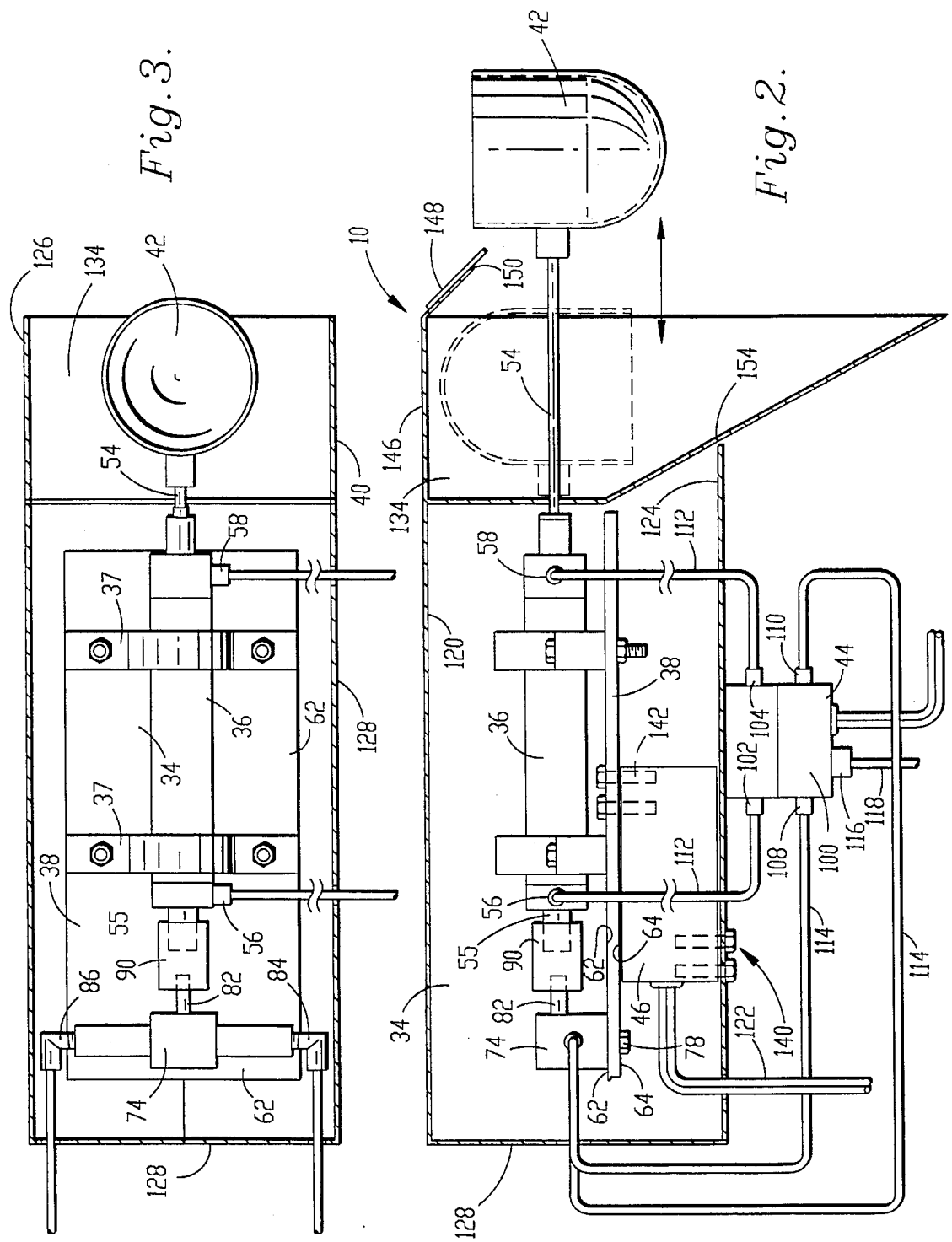

BULK DENSITY SAMPLER APPARATUS

BACKGROUND OF THE INVENTION

1. Field of the Invention

The present invention is broadly concerned with an improved bulk density sampler of the type used for sampling material flowing in a material processing stream. More particularly, it is concerned with such a bulk density sampler which is especially effective and advantageously adapted for continuous density sampling of granular food products during processing.

2. Description of the Prior Art

Food manufacturing processes typically require that food processing operating conditions be closely and continuously monitored to obtain a desired food product. It is often necessary, therefore, to obtain frequent samples from a food processing stream for measurement and analysis, and further, to develop information for processing adjustment and control.

By way of example, in the manufacture of granular dry foods (e.g. cereal, pet food, pasta and snack food), it is desirable that the final density of the food product material fall within a certain specification range. Accordingly, it is essential that the food product stream be continuously sampled and analyzed so that it will be possible to effect the desired density of the food product by making processing adjustments to upstream operating conditions.

In the past, food product streams have been sampled by sampling equipment typically including a sampling cup of known weight which was selectively shuttled between a flowing product stream and a retracted position at which the contents of the cup were dumped on a scale container for weighing. After being weighed, the product being weighed was discarded. Such a weighing system suffered the disadvantage of secondarily handling the product during the weighing step. In addition, because the product would be discarded after being weighed, the food product losses became substantial, especially if the sampling process was continuous.

SUMMARY OF THE INVENTION

The present invention overcomes the problems outlined above and provides a bulk density sampler in the form of a sampling apparatus having a sampling assembly and means for weighing the assembly. The sampling assembly includes a sample receptacle of known volume and a means for selectively shifting the receptacle between a sampling position, in which the receptacle receives a sample from a product stream, and a weighing position, in which the receptacle is positioned outside the material stream. Once in the weighing position, the weighing means weighs the entire sampling assembly and determines sample weight by taring out the empty weight of the sample assembly. Thereafter, the density, a function of product weight for a known volume (i.e. receptacle volume) may be calculated.

The sampling assembly preferably includes a protective cover serving several functions. It shields the receptacle from the product stream when the receptacle is in its weighing position, serves as a scraper apparatus during the shifting of the receptacle between the sampling position and the weighing position, and also functions as a deflector to divert the product stream into the receptacle when the receptacle is in the sampling position. The weighing means preferably includes a tare weight circuit means to compensate for the empty weight of the assembly. A programmable control means is preferably included to provide functionality for continuous sampling on selective frequencies and alarm features. A trend chart is preferably included to provide functionality for trend analysis between successive samples.

BRIEF DESCRIPTION OF THE DRAWINGS

FIG. 1 is a perspective side view of the bulk density sampling apparatus showing the sample receptacle in the product sampling position.

FIG. 2 is a side elevational view of the bulk density sampling apparatus showing the cover in cross-sectional view, with the receptacle shown in the product sampling extended position and also in the inverted position (shown in phantom) for returning the product back to the product stream.

FIG. 3 is a top view of the bulk density sampling apparatus showing the receptacle under the protective cover in its weighting position.

FIG. 4 is a logic diagram of the electrical control system associated with the bulk density sampling apparatus depicted in the several views of the drawings.

DETAILED DESCRIPTION OF THE PREFERRED EMBODIMENT

Turning now to the drawings, there is shown a bulk density sampler apparatus generally designated by the numeral 10. Referring to FIG. 1, there is also shown a farinacious (cereal based) material stream 16 including a vertical portion 20 formed when the material stream 16 flows gravitationally from a first conveyor 24 to a second conveyor 28 disposed thereunder.

The bulk density sampler apparatus comprises a sampling assembly 34 and a weighing means, which in the preferred embodiment is a load cell 46. The sampling assembly 34 includes a double-acting air pressure cylinder 36, bearings 37, a platform 38, a housing assembly 40, a sampling receptacle 42, and an air solenoid assembly 44.

The double-acting air pressure cylinder 36 provides the means for selectively shifting the receptacle 42 between a sampling position and a weighing position. It will be appreciated by those skilled in the art, that other suitable means may be employed for selectively shifting receptacle 42 between sampling and weighing positions, including for example, electrically powered means. The cylinder 36 includes a reciprocating piston (not shown) operative within the pressure cylinder 36 to actuate an axially-extending shaft 54. The shaft 54 is fixedly attached at one end to the piston and at an opposite end to the sample receptacle 42. The cylinder 36 is configured to prohibit the relative rotation between piston and cylinder 36. The cylinder 36 includes a butt end 55, opposite the cylinder end from which shaft 54 extends. The air pressure cylinder 36 is of the type which can be obtained from Bimba Manufacturing Company, Monde, Ill., Model No. 176DXNR. The cylinder 36 is provided with pneumatic ports 56 and 58, each permitting air flow to and from opposite sides of the piston for shifting of the shaft 54 and receptacle 42 between sampling and weighing positions.

Platform 38 is rectangular in shape and presents generally flat, horizontal, upwardly and downwardly facing surfaces 62 and 63, respectively.

A pair of bearings 37 are mounted to platform 38 by conventional threaded fasteners and rotatably receive air pressure cylinder 36. The bearings 37 are of pillow block design and operate to permit rotation of the cylinder 36 within the bearings 37, while maintaining the cylinder 36 and shaft 54 generally parallel to platform upwardly facing surface 62.

A pneumatically-driven rotary actuator 74 is secured to upwardly facing surface 62 of platform 38 adjacent to the butt end 55 of the air pressure cylinder 36 by means of conventional threaded fasteners 78. The rotary actuator 74 includes a horizontal rotary shaft 82 and pneumatic ports 84 and 86. The rotary actuator 74 is of the type which can be obtained from Bimba Manufacturing Company, Monde, Ill., Series 017. The actuator 74 operates to rotatably cycle shaft 82 over a range of 180° when suitable air pressure is supplied to either ports 84 or 86. Actuator 74 is configured so that when it is mounted to platform 38, the longitudinal axis of shaft 82 is in substantial alignment with the longitudinal axis of air cylinder 36.

Shaft 82 is fixedly secured to cylinder butt end 55 by means coupler 90 so that rotational motion of the shaft 82 will be transmitted, through the coupler 90, to air pressure cylinder 36, causing the rotation of cylinder 36 in bearings 37. Coupler 90 is cylindrical in shape and includes a shaft opening 91 and cylinder butt end opening 92. Opening 91 is provided with a keyway (not shown) and is configured for snugly receiving shaft 82 of rotary actuator 74. Rotary shaft 82 of actuator 74 is also configured with a key and keyway (not shown) which corresponds to and cooperates with the keyway in shaft 82 to coupler 90. Butt end opening 92 is configured to snugly receive butt end 55 of cylinder 36 and is secured thereto by means of conventional pins (not shown) so that rotational motion of the coupler 90 will be transmitted to the butt end 55 to cause rotation of cylinder 36.

The air solenoid assembly 44 is configured to selectively direct air pressure to cylinder 36 and actuator 74. Solenoid assembly 44 is provided with a main body 100 having a pair of air cylinder ports 102, 104, and a pair of rotary actuator ports 108, 110. Solenoid assembly 44 is further provided with flexible hoses 112 suitable for the communication of compressed air from solenoid ports 102 and 104 to cylinder ports 56 and 58, respectively. Flexible hoses 112 are of sufficient resiliency and durability to withstand pneumatic line air pressures necessary for extension and retraction of shaft 54. Flexible hoses 112 are also sufficiently resilient and durable and of sufficient length to permit the repeated rotational cycling of air cylinder 36 over a 180° rotational range.

Solenoid assembly 44 is provided with flexible hose 114 which is of sufficient length, durability and resiliency to communicate air pressure to rotary actuator 108 sufficient to rotate shaft 54, coupler 90 and air cylinder 36, and receptacle 42 through their 180° cycle range. The solenoid assembly 44 is further provided with an electrically-driven solenoid 116 which, in response to electric signals carried by cable 118, cooperates with an internal solenoid body valve means (not shown) to selectively direct air pressure from air supply 119 to ports 102, 104, 108, or 110, as desired. Solenoid assembly 44 is configured so that when air pressure is supplied by the solenoid to either ports 108 or 102, corresponding ports 104 and 110 act as exhaust ports providing an exhaust route for air returning from the air cylinder 36 and actuator 74, respectively. Likewise, when the solenoid assembly 44 is aligned to supply air pressure to ports 104 and 110, then ports 102 and 108 act as exhaust ports and provide an exhaust route for air returning from air cylinder 36 and rotary actuator 74. The air solenoid assembly 44 is of the type manufactured by Rexroth of Lexington, Ky., Model 740.

Receptacle 42 is generally cylindrical in shape and in the preferred embodiment has a semi-hemispherical bottom, as shown in FIGS. 2 and 3. It will be appreciated that the operating volume of receptacle 42 will be dictated by the material being sampled and operating space constraints. Receptacle 42 employs a semi-hemispherical bottom rather than a cylindrical bottom to eliminate sites at which sticky products can cling and accumulate. In the event that the material being measured is not sticky or does not tend to build up within the receptacle, it will not be necessary to employ a hemispherical bottom within receptacle 42. Receptacle 42 can also be configured with a slide (not shown) to allow the product to smoothly slide back into the product stream rather than falling out of the receptacle, the latter of which tends to cause hammering or material damage, or both.

In the preferred embodiment, the load cell 46 is a dual cantilevered beam designed for single point platform weighing. Load cell 46 is provided in the form of a load cell such as that available from Cooper Instruments of Warrenton, Vir., Model 662A. The load cell 46 selected for use, however, can be of any design adapted to perform weight measurements and convert the measurement into an electronic signal transmitted over cable 122.

The housing assembly 40 includes a ceiling 120, a floor 124, and three walls 128, each cooperating to define a generally rectangular box-shaped housing which presents an opening 134. Load cell 46 is secured to the housing floor 124 on its bottom-most portion, and at its upper portion to downwardly facing surface 64 of platform 38, as shown in FIGS. 2 and 3. It will be appreciated that the air cylinder assembly 36 and platform 38 are disposed and centered on top of load cell 46 to facilitate weight measurement of the sampling assembly 34 and platform 38, as desired. Further, when so disposed within housing assembly 40, platform 38 is substantially parallel to housing floor 124 so that the stroke of shaft 54 is along a longitudinal axis which is substantially horizontal. When disposed within housing assembly 40, sampling assembly 34 is oriented with the shaft 54 and receptacle 42 extending into and centered within housing opening 134.

Housing ceiling 120 is further provided with a horizontal hood 146 portion extending outwardly from the opening 134 and terminating with an integrally connected, downwardly deflecting shield 148. The hood 146 generally extends over the receptacle 42 when the receptacle 42 is fully retracted and in the weighing position. A slide 154 is disposed beneath the ceiling hood 146 and is fixedly secured to housing floor 124 and extends between opposite walls 128, as shown in FIGS. 2 and 3. The slide 154 is angled downwardly so that when receptacle 42 is inverted, as shown in phantom in FIG. 2, the ejected material falling onto slide 154 will be deflected and returned to the material stream 16.

Deflecting shield 148 presents a lower scraping edge 150 which is substantially horizontal and configured to scrape excess product from the top of receptacle 42 as it is retracted from its sampling position to its weighing position beneath hood 146. The angle of deflection shield 148 is preferably about 45°, but may advantageously be of any angle which is effective to scrape and level product in receptacle 42 when it is being retracted to a weighing position, and further to protect the receptacle 42 while being weighed from particles falling in the material stream 16, which can cause inaccuracies in weight measurement. The housing assembly 40 may be constructed of any material which is effective in protecting the load cell 46 from air current or any falling material, including material from the product stream, or from any other extraneous materials, including water in the operating environment.

The deflection shield 148 in the preferred embodiment is integral with hood 146, but may also advantageously be a separate component secured to hood 146 by any suitable means. Deflection shield 148 may also be provided with means by which its lower scraping edge 150 may be adjusted relative to the travel path of receptacle 42.

Reference will now be made to FIG. 4 where there is shown a logic diagram of the electrical control system. A tare circuit board 158 is provided to create a negative signal equal to a voltage transmitted from load cell 46, which voltage represents the weight of the sampling assembly 34 and platform 38 with the receptacle 42 empty. Thus, when the load cell 46 generates a voltage representative of sampling assembly 34 and platform 38 with receptacle 42 filled with product from material stream 16, and is added to the negative voltage generated by tare circuit board 158, a voltage is generated which is representative of the weight of product within receptacle 42. The tare circuit board 158 in the preferred embodiment consists of a highly accurate differential amplifier with an extended range for offset adjustments.

A programmable controller 160 is provided to control the operation of the bulk density sampling apparatus 10 and to process the data generated from the load cell 46 into usable form. The controller 160 is preferably programmed to take at least one hundred load cell 46 readings in less than one second and to average the readings and generate an output reflecting the average. The number of readings per weight measurement can vary and may consist of any number which is effective to filter out electronic noise within the programmable controller 160 (e.g. noise emanating from the programmable controller 160 internal clock).

The programmable controller 160 is also programmed to generate a density reading based upon the volume of the receptacle 42, which volume is input into the programmable controller 160, along with other information such as density conversional constants, by the operator. The programmable controller 160 displays the density measurement on front panel 162, both numerically and graphically. The graphic display is in the form of a control chart generated by a trend chart apparatus 164. The trend chart apparatus 164 may be used to develop any desired trend chart for use in recording and analyzing trends in the bulk density of the material stream 16. The programmable controller 160 is also advantageously employed to provide an alarm function displayed on panel 162, based upon upper and lower control limits for bulk density, which limits are entered into the programmable controller 160 by an operator.

The programmable controller 160 preferrably includes a compensation feature operable when product from material steam 16 accumulates in the receptacle 42 between samples. Such accumulation typically occurs because, for example, product dust has a propensity to cling to inner receptacle 42 surfaces. If not accounted for, the accumulation of product within receptacle 42 between samples effectively reduces the volume of receptacle 42, which in turn leads to erronious bulk density calculations. (Programmable controller 160 calculates bulk density based upon the weight of receptacle 42 contents divided by receptacle 42 volume, which is assumed to be constant.) Thus, programmable controller 160 is programmed to provide an accumulation compensation function when an increase in empty weight of sampling assembly 34 between samples is detected. The compensation function is operable to reduce the effective volume of receptacle 42, used by programmable controller 160 to calculate bulk density, by an amount which is a function of the weight of the accumulated product within receptacle 42 divided by the density of the accumulated product. If the accumulated product is dust, the density of the dust is predetermined and input into programmable controller 160 for use in the compensation function. The weight of the accumulated product is determined by measurement of the increase in empty weight of the sampling assembly 34 between samples.

In operation to cause assembly 34 to collect a sample, programmable controller 160 generates a signal which is sent to air solenoid assembly 44 on cable 118 to admit air pressure through port 102 to air port 56 of air pressure cylinder 36 through flexible hose 112. At that time, air solenoid assembly 44 aligns internally to exhaust air from port 58 of cylinder 36 through flexible hose 112 to port 104. The air pressure forces the piston within cylinder 36 to extend shaft 54 outwardly so that receptacle 42, in the upright position, will be extended into its sample position in the vertical stream portion 20 of the material stream 16, as shown in FIG. 1. Programmable controller 160 is programmed to keep receptacle 42 in the vertical stream portion 20 for a sufficient amount of time to allow it to be filled. In the preferred embodiment, the programmable controller 160 is programmed so that the receptacle 42 will remain in the vertical stream portion 20 for a period of time fifty percent longer than is required to fill the cup. This insures that the cup is full before retracting the cup for weighing.

After the programmed amount of time passes, programmable controller 160 signals air solenoid assembly 44 to align internally so that air pressure is supplied to port 104 and exhausted from port 102, which in turn causes the retraction of shaft 54 and receptacle 42 to its weighing position. As receptacle 42 is retracted into housing assembly 40, its upper edge is brought into contact with the scraping edge 150 of deflecting shield 148 for the purpose of leveling material contents of receptacle 42. When the sampler apparatus 10 is set up for operation, sampling assembly 34 and cup 42 are oriented so that the upper edge of receptacle 42 is parallel to scraping edge 150. In the preferred embodiment, the edge 150 lies within $\frac{1}{32}$ of an inch above a plane forming the upper edge of receptacle 42. It will be apparent to those skilled in the art that such adjustments are necessary to prevent damage to the deflecting shield 148 or the receptacle 42 by undesirable contact therebetween during the cycling of shaft 54 between its fully extended and fully retracted positions. Once receptacle 42 is fully retracted to its weighing position, as shown in FIG. 3, programmable controller 160 causes load cell 46 and tare circuit board 158 to generate a signal representative of the weight of the contents of receptacle 42. Thereafter, programmable controller 160 sends a signal to solenoid assembly 44 which causes air pressure to be supplied through port 108 and exhausted through port 110, which in turn causes actuator 74 to rotate sampling assembly 34 through a range of 180°, so that receptacle 42 is in the inverted position, as shown in phantom in FIG. 2. It will be appreciated that flexible hoses 112 are to be of sufficient length and orientation to allow the sampling assembly to rotate as described without becoming entangled.

The material ejected from the inverted receptacle 42 falls onto slide 154 which directs the product back into the material stream 16. In the alternative, programmable controller 160 may be programmed to fully extend shaft 54 back into the vertical stream portion 20 before inverting receptacle 42. This allows the contents of receptacle 42 to be returned directly to the product stream 16.

The programmable controller 160 next sends a signal to air solenoid assembly 44 to supply air to port 110 and exhaust air from port 108, causing sampling assembly 34 and receptacle 42 to rotate 180° in the reverse direction so that receptacle 42 is returned to the upright position.

Programmable controller 160 may be programmed to sample bulk density at any desired frequency.

As described above, the instant invention provides an apparatus which avoids secondary product handling and product losses because the entire sampling assembly 34 is weighted after sampling. The instant invention also provides an apparatus with programmable features not found in the prior art and which detect, alarm and compensate for product accumulation within the sampling receptacle, which can lead to error bulk density measurement if not taken into consideration. The instant invention yet further provides an apparatus which is configured to allow the receptacle 42 to dump its contents either in the product stream directly or, in the alternative, onto a slide positioned within the sampling assembly which deflects the ejected product from the receptacle 42 back into the product stream.

Having described the preferred embodiments of the present invention, the following is claimed as new and desired to be secured by Letters Patent.

We claim:

1. A bulk density sample apparatus for sampling material in a material stream comprising:

a sampling assembly including
      a sample receptacle of known volume, and shifting means coupled with said receptacle for selectively shifting said receptacle between a sampling position in which said receptacle is positioned in the material stream for receiving a sample thereof and a weighing position in which said receptacle is positioned outside the material stream; and weighing means for determining the weight of a material sample
      received in said receptacle and for using said weight and known volume for determining the bulk density of the material sample, said weighing means being positioned for supporting and carrying the weight of said assembly including both said receptacle and shifting means and operable for weighing said assembly for determining the difference between a gross weight of said assembly when said receptacle contains a sample and a tare weight when said receptacle contains a sample and a tare weight when said receptacle is empty, said difference being said weight of the material sample, said sampling assembly including a deflector shield adapted to level material in said receptacle as said receptacle is shifted between said sampling position and said weighing position.

2. The apparatus of claim 1, said weighing means including tare weight means adapted to subtract empty weight of said assembly from the weight of said assembly when said receptacle is filled with a sample for determining the weight of the sample in said receptacle.

3. The apparatus of claim 2, said weighing means including means for comparing empty weights of said assembly between material samplings and for activating an alarm when the difference between selected successive empty weights exceeds a predetermined limit for determining undesirable material accumulation in said receptacle.

4. The apparatus of claim 1, said weighing means including means for measuring material density by calculating density as a function of weight of material in said receptacle and receptacle volume.

5. The apparatus as set forth in claim 4, said weighing means including a trend chart apparatus adapted to display trends in density measurements.

6. The apparatus as set forth in claim 1, said weighing means adapted to perform multiple weight measurements of said assembly and receptacle contents for each material sampling.

7. A bulk density sample apparatus for sampling material in a material stream comprising:

a sampling assembly including:
      a sample receptacle of known volume, and means for selectively shifting said receptacle between a sampling position in which said receptacle is positioned in the material stream for receiving a sample thereof and a weighing position in which said receptacle is positioned outside the material stream; and means for weighing said assembly including said receptacle, said sampling assembly including a deflector shield adapted to level the material in said receptacle as said receptacle is shifted between said sampling position and said weighing position, said deflector shield angled at about 45° relative to a horizontal plane for protecting said receptacle from the material stream while in said weighing position.

8. The apparatus of claim 1, said shifting means adapted to return material in said receptacle to the material stream by inverting said receptacle directly into the material stream.

9. The apparatus of claim 1, said shifting means adapted to return the material in said receptacle to the material stream by inverting said receptacle after being weighed in its weighing position and ejecting by gravity flow the receptacle contents onto a slide which deflects the material into the material stream.

10. The apparatus of claim 1, said weighing means including means for measuring material density by calculating density as a function of weight of material in said receptacle and receptacle volume.

11. The apparatus of claim 10, said weighing means including a trend chart apparatus adapted to display trends in density measurements.

12. The apparatus of claim 1, said weighing means adapted to perform multiple weight measurements of said assembly and receptacle contents for each material sampling.

13. A bulk density sampler apparatus for sampling material in a material stream comprising:

a sampling assembly including
      a sample receptacle of known volume, means for selectively shifting said receptacle between a sampling position in which said receptacle is positioned in material stream for receiving a sample thereof and a weighing position in which said receptacle is positioned outside the material stream, and
      a deflector shield for leveling the material in said receptacle as said receptacle is shifted between said sampling and weighing positions, said shield angled at about 45° relative to a horizontal plane for protecting said receptacle from the material stream while in said weighing position, and means for weighing said assembly including said receptacle,
      said weighing means including
         tare weight means adapted to subtract empty weight of said assembly from weight of said assembly when said receptacle is filled with a sample for determining the weight of the sample in said receptacle, said weighing means adapted to compare empty weights of said assembly between material samplings and to activate an alarm when the difference between selected successive empty weights of said assembly exceeds a preset limit, said comparison for determining undesirable material accumulation in said receptacle, said weighing means including means for measuring material density by calculating density as a function of the weight of the sample in said receptacle and receptacle volume, said weighing means including means for producing a trend chart for displaying trends in said material density, and said weighing means adapted to perform multiple weight measurements of said assembly and thereby said receptacle contents for each material sample.

14. The apparatus as set forth in claim 1, said weighing means including a load cell positioned for supporting and carrying the weight of said assembly and for producing signals representative thereof.

15. A bulk density sample apparatus for sampling material in a material stream comprising:

a sampling assembly including a sample receptacle of known volume, and shifting means coupled with said receptacle for selectively shifting said receptacle between a sampling position in which said receptacle is positioned in the material stream for receiving a sample thereof and a weighing position in which said receptacle is positioned outside the material stream; and weighing means for determining the weight of a material sample received in said receptacle and for using said weight and known volume for determining the bulk density of the material sample, said weighing means being positioned for supporting and carrying the weight of said assembly including both said receptacle and shifting means and operable for weighing said assembly for determining the difference between a gross weight of said assembly when said receptacle contains a sample and a tare weight when said receptacle contains a sample and a tare weight when said receptacle is empty, said difference being said weight of the material sample, said shifting means including a fluid-operated cylinder having a shiftable cylinder rod extending therefrom with the distal end thereof coupled with said receptacle.

16. The apparatus of claim 15, said weighing means including tare weight means adapted to subtract empty weight of said assembly from the weight of said assembly when said receptacle is filled with a sample for determining the weight of the sample in said receptacle.

17. The apparatus of claim 16, said weighing means including means for comparing empty weights of said assembly between material samplings and for activating an alarm when the difference between selected successive empty weights exceeds a predetermined limit for determining undesirable material accumulation in said receptacle.

18. The apparatus of claim 15, said weighing means including means for measuring material density by calculating density as a function of weight of material in said receptacle and receptacle volume.

19. The apparatus as set forth in claim 18, said weighing means including a trend chart apparatus adapted to display trends in density measurements.

20. The apparatus as set forth in claim 15, said weighing means adapted to perform multiple weight measurements of said assembly and receptacle contents for each material sampling.

21. A bulk density sample apparatus for sampling material in a material stream flowing through a conduit comprising:

structure configured for creating a material-free zone within the conduit;

a sampling assembly including a sample receptacle of known volume, shifting means for selectively shifting said receptacle between a sampling position in which said receptacle is positioned in the material stream for receiving a sample thereof and a weighing position in which said receptacle is positioned in said material-free zone and within said conduit; and weighing means for determining the weight of a material sample received in said receptacle and for using said weight and known volume for determining the bulk density of the material sample.

22. The apparatus as set forth in claim 21 said structure including a deflection shield presenting an angle relative to a horizontal plane and having a leading edge positioned for leveling material received in said receptacle as said receptacle shifts from said sampling position to said weighing position.

23. The apparatus as set forth in claim 20, said deflection shield presenting an angle of about 45° relative to a horizontal plane.

24. The apparatus as set forth in claim 21, said weighing means including a load cell positioned for supporting and carrying the weight of said assembly including both said receptacle and shifting means and for producing signals representative of the weight of said assembly.

25. The apparatus as set forth in claim 21, said shifting means including a fluid-operated cylinder having a longitudinally shiftable cylinder rod extending therefrom and extending through a hole defined in the conduit with the distal end thereof positioned within the conduit coupled with said receptacle for shifting said receptacle within the conduit between said sampling and weighing positions.

* * * * *